(12) United States Patent
Göbel (10) Patent No.: US 11,185,401 B2
(45) Date of Patent: Nov. 30, 2021

(54) BLADDER CATHETER FOR THE MINIMALLY INVASIVE DISCHARGE OF URINE

(71) Applicant: Creative Balloons GmbH, Waghäusel (DE)

(72) Inventor: Fred Göbel, Wilhelmsfeld (DE)

(73) Assignee: Creative Balloons GmbH, Waghäusel (DE)

( * ) Notice: Subject to any disclaimer, the term of this patent is extended or adjusted under 35 U.S.C. 154(b) by 944 days.

(21) Appl. No.: 15/533,141

(22) PCT Filed: Dec. 4, 2015

(86) PCT No.: PCT/IB2015/002282
§ 371 (c)(1),
(2) Date: Jun. 5, 2017

(87) PCT Pub. No.: WO2016/087926
PCT Pub. Date: Jun. 9, 2016

(65) Prior Publication Data
US 2017/0325927 A1 Nov. 16, 2017

(30) Foreign Application Priority Data
Dec. 4, 2014 (DE) ..................... 10 2014 017 873.0

(51) Int. Cl.
*A61F 2/00* (2006.01)
*A61M 25/00* (2006.01)
*A61M 25/10* (2013.01)

(52) U.S. Cl.
CPC ....... *A61F 2/0027* (2013.01); *A61M 25/0017* (2013.01); *A61M 25/1002* (2013.01);
(Continued)

(58) Field of Classification Search
CPC ............. A61F 2/0027; A61M 25/0017; A61M 25/1002; A61M 25/10188; A61M 25/0097; A61M 2025/0056; A61M 2025/105; A61M 2025/1065; A61M 2025/1068; A61M 2025/1072
(Continued)

(56) References Cited

U.S. PATENT DOCUMENTS 5,306,226 A * 4/1994 Salama ................. A61F 2/0009
128/DIG. 25
5,360,402 A * 11/1994 Conway ................. A61L 29/06
604/915
(Continued)

FOREIGN PATENT DOCUMENTS

DE 3742710 7/1989
DE 102011110778 1/2013
(Continued)

*Primary Examiner* — Andrew J Mensh
(74) *Attorney, Agent, or Firm* — Pandiscio & Pandiscio (57) ABSTRACT

The invention relates to devices (1) for draining or closing a natural or artificial bladder outlet by means of a balloon body (3) made of preferably micro-scale thin-walled Polyurethane, which has a vesical anchor, is transurethrally sealing and is extended into the urethra or through the urethra. According to the invention, the balloon body is seated on a shaft body (2) supporting the balloon, and the filling of the balloon body is preferably done with air.

39 Claims, 8 Drawing Sheets

(52) U.S. Cl.
CPC ... *A61M 25/0097* (2013.01); *A61M 25/10188* (2013.11); *A61M 2025/0056* (2013.01); *A61M 2025/105* (2013.01); *A61M 2025/1065* (2013.01); *A61M 2025/1068* (2013.01); *A61M 2025/1072* (2013.01)

(58) Field of Classification Search
USPC .......................................................... 604/544
See application file for complete search history.

(56) References Cited

U.S. PATENT DOCUMENTS

| | | | | |
|---|---|---|---|---|
| 5,441,485 | A * | 8/1995 | Peters | A61M 25/1002 604/101.01 |
| 6,102,929 | A * | 8/2000 | Conway | A61M 25/0075 606/192 |
| 2008/0125757 | A1* | 5/2008 | Gobel | A61M 25/0017 604/544 |
| 2009/0030370 | A1* | 1/2009 | Nishtala | A61M 25/04 604/103.01 |
| 2010/0022976 | A1* | 1/2010 | Weig | A61F 5/451 604/355 |
| 2010/0113939 | A1* | 5/2010 | Mashimo | A61B 5/02158 600/470 |
| 2011/0218389 | A1* | 9/2011 | Gobel | A61M 27/00 600/32 |

FOREIGN PATENT DOCUMENTS

| | | |
|---|---|---|
| WO | WO 2007/005734 | 1/2007 |
| WO | WO 2008/038172 | 4/2008 |
| WO | WO 2011/139498 | 11/2011 |

* cited by examiner

BLADDER CATHETER FOR THE MINIMALLY INVASIVE DISCHARGE OF URINE

REFERENCE TO PENDING PRIOR PATENT APPLICATIONS

This patent application claims benefit of International (PCT) Patent Application No. PCT/IB2015/002282, filed 4 Dec. 2015 by Creative Balloons GmbH for BLADDER CATHETER FOR THE MINIMALLY INVASIVE DISCHARGE OF URINE, which claims benefit of German Patent Application No. DE 10 2014 017 873.0, filed 4 Dec. 2014, which patent applications are hereby incorporated herein by reference.

FIELD OF THE INVENTION

The invention is directed to a device in the form of a tube or catheter for draining or sealing a natural or artificial bladder outlet, comprising a shaft body that can be applied extracorporeally into the bladder as well as a balloon that surrounds it like a cuff for the vesical anchoring of the shaft body in the bladder.

BACKGROUND OF THE INVENTION

Indwelling bladder catheters for the continuous, closed discharge of urine from a patient's bladder exist in many different embodiments as a part of standard medical care.

Indwelling bladder catheters are usually inserted into the bladder by trans-urethral catheterization. In contrast to catheterization of the bladder with disposable catheters, in which a urine-discharging catheter shaft is intermittently advanced through the urethra into the bladder lumen, catheters for long-term catheterization are typically equipped with a balloon-like anchor element (retention balloon) at their distal end that comes to rest in the interior of the bladder.

In the majority of indwelling bladder catheters, these retention balloons consist of an elastically stretchable tubing material, which fits snugly and rests on the shaft body of the catheter without any pre-formation. When filled with a medium, which is normally a liquid, and with a sufficient application of force, a spherical balloon body expands out of the cylindrical tube component, usually in a spherical shape. A disadvantage of anchor balloons of this type, which are expanded under high pressure, is primarily the hard consistency of the balloon that sets in. For longer durations of catheterization, it is not uncommon to observe structural damage to the bladder mucosa in the contact area of the balloon in the region of the so-called bladder trigone. Some of this damage can develop into long-lasting ulcerations and can be the source of chronic inflammation of the urinary tract if bacterial contamination occurs.

The present invention is based on a catheter design that is already described in part in WO2008/038172.

The "indwelling urinary catheter with enlarged sealing surface" disclosed there describes a catheter balloon that is already pre-shaped to its working dimensions during manufacture and that, once placed in the bladder, rests upon the catheter shaft in an only incompletely filled, flaccid state. Owing to the specific, slight volumetric expandability of the balloon envelope, the balloon cannot deform to a circumference that would permit it to slip out or emerge through the urethra when external axial tensile force acts on the anchor balloon. Instead, if it is pulled from outside, the balloon that anchors the catheter in the trigone of the bladder assumes the shape predetermined during manufacture. It does not deform, and pressure approximately corresponding to the tensile force acting upon it develops inside it. As the pulling effect subsides, the pressure in the balloon interior returns to the physiological pressure prevailing in the bladder. The proposed design thus permits a nearly pressure-neutral effect by the balloon on the tissue adjacent to it. Lesions, such as those caused by conventional balloon bodies that are completely filled, can largely be prevented by the described design.

A problem associated with the placement of indwelling bladder catheters is ascending infections or colonizations of the bladder interior by germs, which reach the bladder via the patient's urethra, basically following the unphysiological surface of the catheter shaft, several days after the catheter has been inserted.

Although the pressure-neutral seal of the bladder outlet region described in WO2008/038172 permits improved protection from bacterially colonized lesions or ulcerations of the bladder wall, the problem of infections ascending to the bladder through the urethra in patients with indwelling catheters is not solved satisfactorily.

SUMMARY OF THE INVENTION

Accordingly, the objective of the present invention is to improve indwelling bladder catheters for long-term placement in the bladder such that the risk of the bladder being colonized by germs can be reduced overall.

To this end, the forces transmitted to the bladder wall by the anchored balloon in the bladder should be minimized, and the contact surface of the anchored balloon on the bladder wall should be configured such that lesions caused by the effects of force at particular points, as is typical with conventional catheters, can be prevented to the greatest extent possible.

Moreover, a clearly improved seal should be achieved for the gap space between the urine-discharging shaft of the catheter and the mucosa of the urethra.

The proposed catheter devices for the combined sealing of the bladder trigone and the urethra are preferably filled with air rather than with a liquid medium. The filling pressures lie in the low millibar range and do not exceed the physiological pressure prevailing in the patient's bladder, and their effect is thus conceptually pressure-neutral.

To prevent ascending infections, the present invention discloses that the proximal end of the retention balloon that anchors the catheter in the bladder is elongated into or through the urethra.

The gap that forms between the catheter shaft and the urethral wall in conventional catheterization normally fills with heavily germ-infested secretions. In the proposed tamponade of the urethral lumen with a urethral balloon extension with preferably micro-thin walls, the residual gap space between the catheter shaft and the urethra is closed as much as possible. Here the sealing "tamponade" of the urethral lumen is created by largely neutral forces. The intra-abdominal pressure prevailing in the bladder is taken on by the vesical portion of the balloon body and used for the space-filling closure of the urethral lumen. Within the scope of the preferred application of the invention, it follows that only prevailing, physiological forces are active in the body.

The vesical portion of the claimed balloon body is preferably bulbous or conical, wherein the tip of the bulb, or cone, is oriented toward the trigone of the bladder so that, when partially filled, it can snugly fit as well as possible in the respective situs of the bladder outlet. The urethral portion of the balloon body is preferably provided with a "residual" diameter that exceeds the diameter of the urethral lumen by ca. 0.5 to 1.5 times, preferably by 0.5 to 1.0 times. The urethral balloon portion with its oversized diameter thus lies against the urethral wall and forms a radially oriented fold in the residual envelope. The residual diameter over the longitudinal extent of the urethra can compensate for diameter changes in the urethral lumen. The excess size ensures that all parts of the urethra can be tamponaded without requiring a high-force expansion of the balloon envelope. The anchoring and sealing balloon according to the invention is preferably filled with an incomplete or partial filling volume, which is dimensioned such that the balloon body as a whole remains in a flaccid state of expansion, i.e. that the balloon wall is not exposed to a permanent expanding force.

As an alternative embodiment of the present invention, the urethral portion of the balloon body can be dimensioned such that it corresponds to or falls just below the diameter of the respective urethra. In contrast to the residually dimensioned embodiment, the urethral balloon envelope transitions to a completely erect state during filling without the formation of radial invaginations.

As an alternative to partial filling, the balloon body can also be filled with a volume that corresponds to or slightly exceeds the volume of the freely shaped balloon.

The claimed catheter is filled preferably with a gaseous medium and/or with air. The filling medium is supplied preferably via a supply line integrated into the wall of the balloon-supporting shaft. Alternatively, the filling can also take place via a feed line that opens directly into the proximal end of the balloon body and is thus not integrated into the catheter shaft. The feed line can likewise be passed through the gap between the proximal end of the balloon shaft and the outer surface of the shaft. The feed line preferably has a terminal one-way valve, which opens when a filling syringe is applied and automatically closes when the syringe cone is removed. Using a filling syringe to fill with a defined volume ensures the preferred filling of the catheter balloon in an incompletely filled, untensioned state. When the balloon is completely filled or if it is filled beyond the freely unfolded balloon volume, the filling pressure that arises in situ can be slightly manometrically controlled by the user as required.

Furthermore, the feed line can have a permanently integrated manometric pressure display, which permits continuous monitoring of the prevailing filling pressure. This type of display makes it possible to identify, for instance, relative changes in the intra-abdominal pressure prevailing in the bladder interior.

When appropriately thin-walled balloon materials are used, the folding that can occur in the urethral portion of the proximally elongated balloon effectively prevents a free discharge of urine, even at the lowest filling pressures. In particular, the seal is established even when intra-abdominal pressure values are normal, i.e. on the order of magnitude of approximately 10 mbar or 5 to 7 mmHg. As was mentioned above, the claimed catheter, when appropriately incompletely filled, can take on a close absolute approximation of the diagnostically and therapeutically important intra-abdominal pressure in the bladder interior.

The extensive elimination of secretion-accumulating spaces in the urethra, once it is tamponaded according to the invention additionally, has an advantageous effect on the efficiency of optional antibacterial coatings on the balloon surface. On the one hand, the amount of germ-laden secretions is reduced; on the other hand, the remaining film of secretions is exposed to a residually enlarged, antibacterial surface.

The use of maximally thin-walled balloon elements, preferably manufactured by blow-molding from pre-extruded tubing, is excellent for providing flat surfaces, which optimally reduce the overall surface area of the balloon body that is vulnerable to colonization. This is possible as a result of the high radial and axial stretching that acts on the tube blank during molding, optimally levels out the surface irregularities in the wall and leads to almost perfectly flat surfaces when stretched to the micro-thin range. Therefore, extremely thin-walled PUR balloons are favored for the invention.

Apart from reducing germ-laden reservoirs between the urethra and catheter shaft to the greatest extent possible, the claimed extension of the proximal balloon end into the urethra or through the urethra permits improved protection from direct mechanical irritation and lesions of the epithelium by the catheter shaft, which are not uncommon in conventional long-term catheterization.

The claimed seal of the urethral lumen by a sealing, thin-walled balloon, which lies flat against the urethral epithelium, further allows for especially small-bore, atraumatic embodiments of the draining shaft portion of the catheter device. For example, the shaft can be made of polyurethane (PUR), and in this case is preferably manufactured from materials with Shore hardness of 60 A to 90 A, especially preferably from materials in the hardness range 70 to 85 A. The outer diameter of the draining shaft preferably measures 2 to 6 mm, especially preferably 3 to 5 mm. When the stated PUR hardnesses are used, the wall thickness is preferably 0.1 to 0.5 mm, especially preferably 0.15 to 0.3 mm.

To further reduce the outer diameter of the urine-discharging shaft element, the balloon body can be filled through a direct access to the balloon that is produced on the proximal end of the urethral balloon extension. In this way, a shaft-integrated feed line for filling the balloon can be omitted for the purpose of achieving the largest possible drainage lumen with the smallest possible shaft outer diameter.

In addition to balloon bodies consisting of a single continuous balloon envelope, balloon compartments that attach to a vesical balloon in the proximal direction can also be constructed of separated molded balloon elements, which are arranged together in direct succession. They are preferably connected together and permit the respective compartments to be filled such that they communicate with each other.

Of particular importance in preventing bacterial infections in the bladder of a patient with an indwelling catheter is also the accumulation of urine, which collects around a vesical balloon portion that extends into the bladder interior and which "pools" below the distal discharge opening of the catheter shaft. To prevent the formation of such "swamps" and to avoid residual urine, the invention proposes applying the vesical balloon portion to the bladder floor as a flat disc, if possible, and that the balloon portion should be provided with a funnel-like outlet, which is inverted into the distal balloon radius and which extends preferably 3 to 8 mm below the distal balloon radius and transitions there into the urine-discharging catheter shaft. It is conceptually preferred that the transition to the discharging shaft should be at the level of the transition by the bladder floor into the urethra. The funnel-like inversion should be shaped such that it also remains open in the event of axial tension on the catheter shaft and that the distal balloon portions do not close over the funnel base. The funnel outlet can optionally be reinforced by a correspondingly shaped film element that stabilizes the funnel shape.

To optimize the manufacturing effort required for a claimed catheter, other embodiments are possible in which both the shaft and the balloon are formed from a single material blank. In this way, one balloon end is conceptually inverted through the other. The radial stability and kink-free flexibility of the discharging shaft element produced by means of shaping can be optimized advantageously by a wavy corrugation.

BRIEF DESCRIPTION OF THE DRAWINGS

Further features, properties, advantages and effects based on the invention arise from the following description of several embodiments of the invention and with the aid of the accompanying drawing.

The following is shown:

FIG. 3c a further embodiment of the device described in FIG. 3a;

DETAILED DESCRIPTION OF THE PREFERRED EMBODIMENTS

Figure 1:
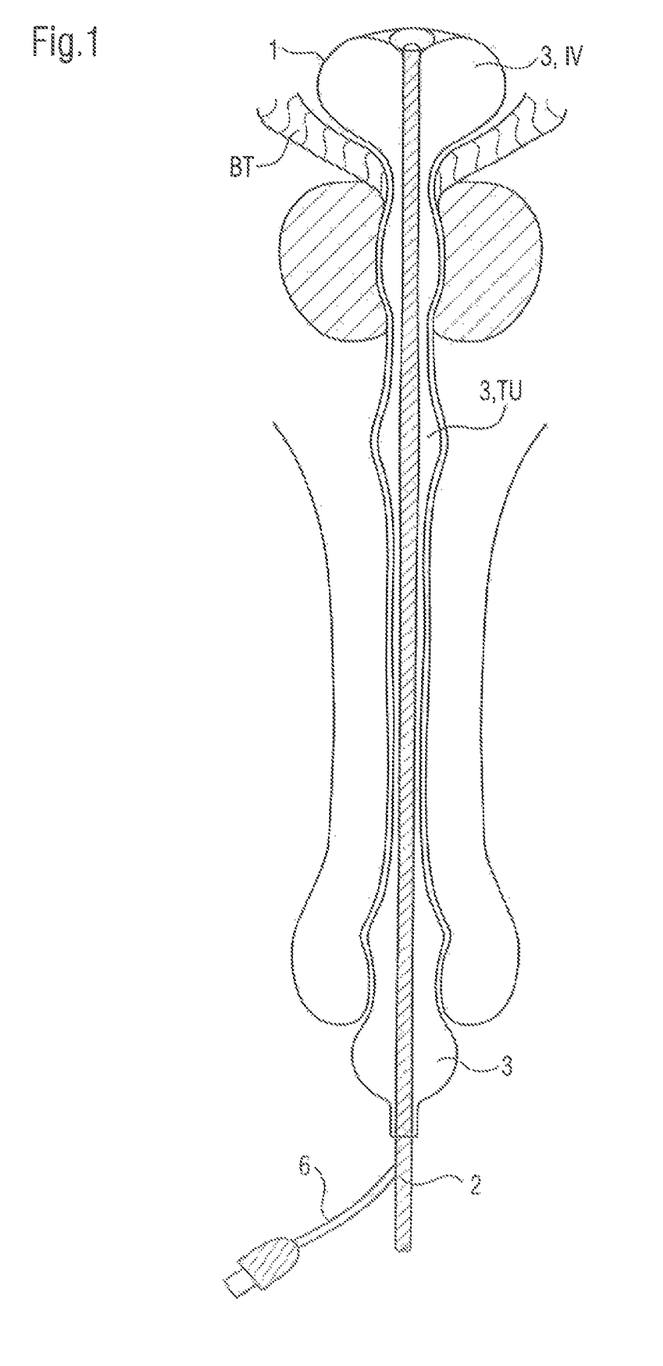
FIG. 1 an embodiment variant of the device with transurethral placement in the male urethra.

FIG. 1 shows a sectional view through a male urinary tract, with a transurethrally placed device 1 according to the invention in the form of an indwelling bladder catheter with a catheter shaft. In this embodiment, the shaft body 2 of said shaft is covered by a balloon 3, which surrounds the shaft body 2 like a cuff over its entire vesical and urethral extent.

Preferably, all sections of the balloon 3—both in the vesical region and in the urethral region—are completely formed to the working dimensions that are necessary for the untensioned tamponade of the particular hollow organ. In an especially preferred embodiment, the diameter in the urethral region slightly exceeds the diameter of the urethra. The anchoring and sealing balloon 3 has a bulbous or conical expansion in its intravesical portion IV. According to the invention, configurations of the balloon are preferred that permit the balloon to fit into the outlet portion of the bladder such that it seals as large an area as possible and in this way, in addition to subjecting the bladder trigone BT to force that is as uniform and atraumatic as possible, permit the most efficient seal possible with the lowest possible filling pressure.

The urethra-side end of the balloon element 3 transitions into a streamlined urethral extension TU. As is shown here, the urethral extension can extend over the entire length of the urethra and beyond the outer ostium.

The diameter ratio of the vesical expansion IV to the urethral extension TU is preferably 2:1 to 6:1, especially preferably 3:1 to 4:1. The wall thickness in the region of the intravesicular expansion IV is preferably 5 to 30 micrometers, especially preferably 10 to 15 micrometers. In the transurethral segment TU, the balloon is preferably 10 to 30 micrometers, and especially preferably 12 to 20 micrometers.

In the embodiment shown, the balloon element 3 is filled through a filling channel, which is integrated into the catheter shaft and transitions to a tube-like filling line 6 at the proximal end of the shaft. For the greatest possible reduction of the filling pressure or of the forces exerted on the adjacent tissue by the device, the balloon body is filled only incompletely, e.g. to 60 to 80% of its freely formed and unpressurized volume. The conceptually preferred flaccid or untensioned property of the balloon 3 filled in this way permits the flaccid balloon envelope to nestle intravesicularly against the individually distinct wall of the outlet portion of the bladder in a way that creates an optimal seal. The pressure taken on intravesicularly from the flaccidly filled balloon 3 has a sealing effect over the surface in the urethral segment TU of the balloon 3. Ideally, the lower urinary tracts can thereby be sealed while placing the catheter in a way that is nearly pressure-neutral overall.

The balloon 3 can be filled both with gaseous and with liquid media.

In the preferred polyurethane embodiment of the balloon element 3, gaseous media, such as ambient air, offer the further advantage of tissue-conserving compressibility. Additionally, in contrast to liquids, they can be applied easily and can also be monitored and adjusted with the aid of a pressure regulator.

The urethral extension TU can project directly out of the vesical segment 4 of the balloon 3, but it can also be affixed to the vesical balloon in the proximal extension as a structurally independent compartment. The vesical balloon segment 4 and the adjoining urethral balloon segment 5 are then communicatingly connected with each other.

In a sequential arrangement such as this, various materials can optionally also be combined. If required, extremely thin walls in the range of 5 to 10 micrometers can also be produced in the urethral balloon section 5, and they correspondingly improve the urethral sealing performance over the wall thickness-related seal that is achieved by molding from a single blank.

In addition to polyurethane, the balloon element 3 can be manufactured from comparably thin-walled soft films, alternative materials such as polyethylene, polyvinyl chloride or TPE-based basic materials. However, the specific properties of polyurethane with a Shore hardness of 70 A to 95 A are preferred, and Shore hardness of 85 A to 90 A are especially preferred. The production is preferably carried out by blow molding pre-extruded tubing material. Coextruded starting materials, which combine e.g. PUR and PVC in a coaxially extruded way, can also be considered for the blow molding.

Figure 2A:
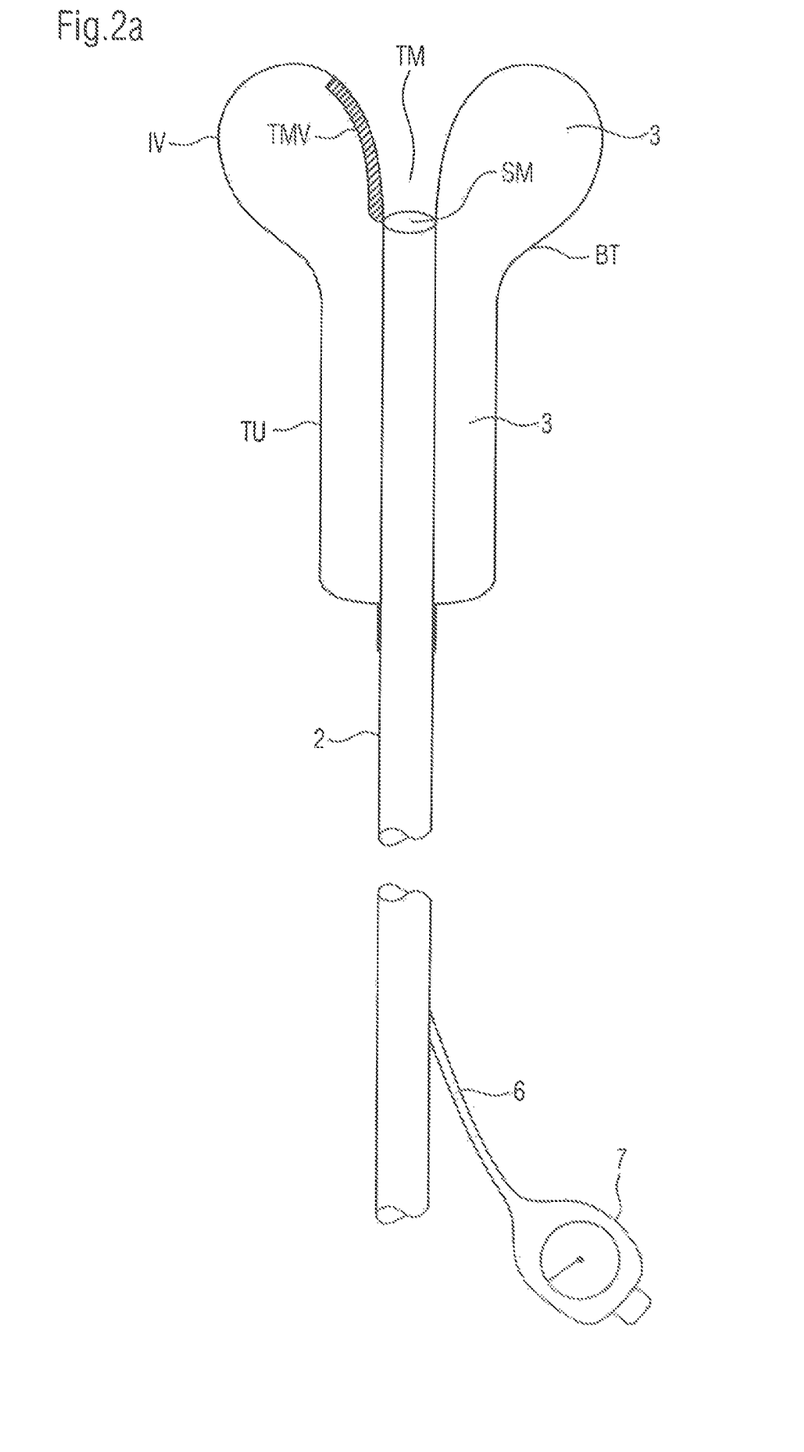
FIG. 2a a preferred embodiment with free deployment of the balloon, wherein the balloon body has a conical or cone-like shape in the transition from the intravesical to the transurethral segment, and the urethral portion extends into the upper portion of the urethra.

FIG. 2a presents a preferably molded balloon body 3 that is freely deployed. Here the intravesical portion IV of the balloon 3 tapers conically in the transition area toward the transurethral extension TU of the balloon 3. In this particular embodiment for the male urethra, the transurethral extension TU extends only up to the transition from the upper third to the central third of the urethra.

The distal end of the balloon is preferably provided with a funnel-like inversion TM, the outlet SM of which is positioned approximately at the level of the transition or bladder trigone BT when filled and placed in the vesicle. The stability of the funnel formation can be stabilized by a separate funnel-like element TMV consisting, for example, of reinforcing film.

In this instance, the filling line 6 to the catheter balloon is provided with a display mechanism 7 at its free end that displays the filling pressure and allows changes to be made in vesicular, and largely analogously, in intra-abdominal pressure in a simple way. For this purpose, the balloon is preferably filled with an incomplete filling volume, which leaves the balloon in a flaccid and unexpanded state, which in turn allows it to accurately take on the respective prevailing vesical and intra-abdominal pressures. The device can thus be used as a technically simple alternative to systems with complex designs for measuring the absolute intra-abdominal pressure and can display relative changes in pressure in the abdomen.

Figure 2B:
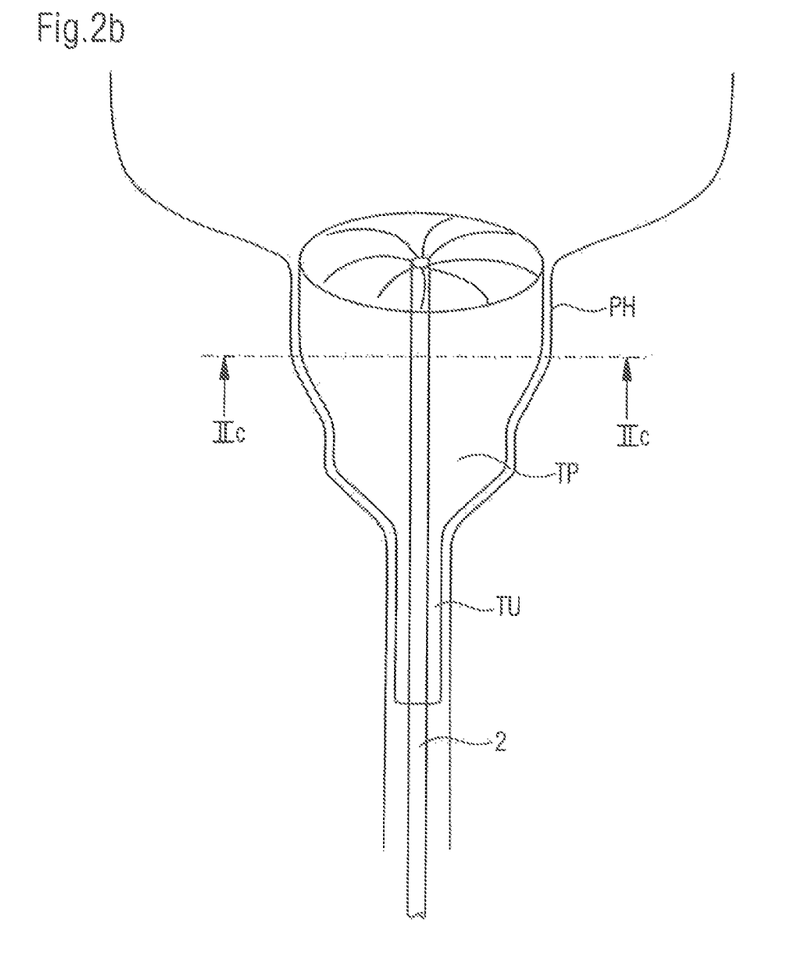
FIG. 2b a particular embodiment of the balloon body with the balloon freely deployed, wherein the balloon body does not form a bearing surface in the region of the bladder floor or trigone, and is instead positioned within a prostate resection cavity, and transitions from there into a portion of the balloon that is positioned urethrally or transurethrally.

FIG. 2b shows an embodiment of the balloon body 3, in which said balloon body does not form a particular bearing surface in the region of the bladder floor or trigone, but is instead positioned within a prostate resection cavity PH, and transitions from there into a balloon segment TU that is positioned in the urethra. The balloon portion TP that is molded for placement in the cavity formed after the resection of the prostate nestles against the situs in a space-filling way. The balloon portion TP is preferably dimensioned such that it exceeds the measurements of the respective prostate resection cavity and that it lies folded against the wall of the respective cavity in such a way that it is optimally untensioned while also providing an optimal seal.

This embodiment is advantageous primarily for patients whose bladders close insufficiently as a result of a resection or in whom urine permanently penetrates into the resection cavity and from there drains into the urethra. In order to optimize the untensioned snug fit of the balloon envelope in the prostate cavity, the balloon portion TP can be provided with an axially attached, bellows-like profile TPF. Resection cavities with irregularly shaped diameters can thus be tamponaded in a particularly advantageous way with a dynamic effect on the structures abutting the balloon that is as homogeneous as possible. If the external sphincter of the bladder is also affected in addition to the internal sphincter, the insufficient closure caused by this can be efficiently sealed by the urethral extension TU of the balloon body, which is elongated beyond the structures of the pelvic floor.

Figure 2C:
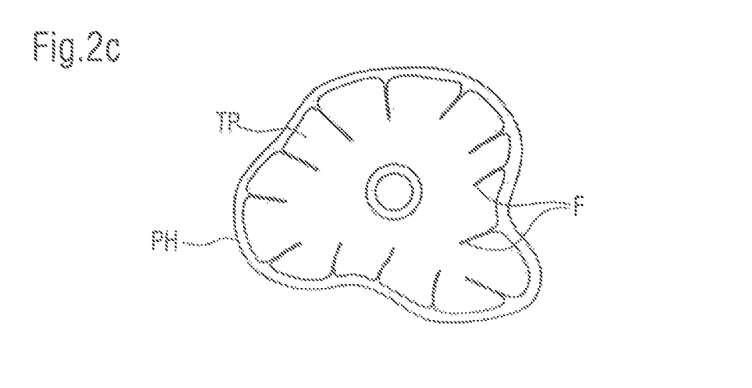
FIG. 2c a horizontal section of a balloon segment described in FIG. 2b for the tamponade of a surgically created prostatic fossa FIG. 3a a single-lumen shaft variant, wherein the transurethral segment of the balloon body extends beyond the outer urethral opening and is filled directly from the proximal end of the balloon body.

FIG. 2c shows the fold F in the residually dimensioned balloon envelope TP, which is accommodated in the transversal section when positioned in the prostate cavity. In particular for prominent structures that protrude into the fossa or for parts of the cavity wall, a uniformly efficiently sealing tamponade of the resection cavity can be established by the residual sizing of the balloon.

Figure 3A:
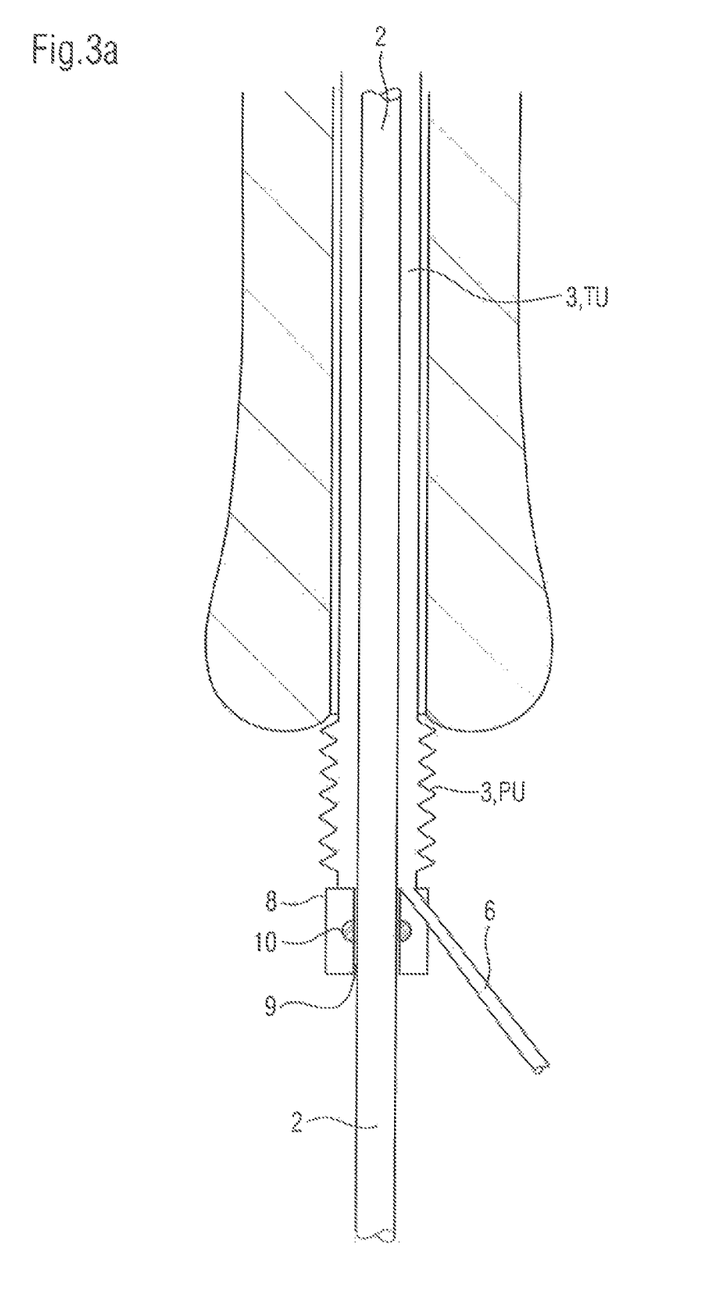

FIG. 3a describes an embodiment of the invention in which the proximal end of the urethral balloon segment PU projects beyond the outer end of the urethra. The balloon element 3 is filled through a feed line here, which is connected directly to the extracorporeal, proximal end of the urethral balloon segment PU. The balloon envelope is closed proximally by a separate element 8, which closes the balloon 3 in the proximal direction and which is clamped into the proximal end of the envelope PU. The closure element 8 has an opening 9 that sealingly accommodates the urine-discharging catheter shaft 2. The opening 9 itself can be provided with a lip-like or ring-like sealing element 10, which makes the closure element, as well as the pre-urethral balloon end PU attached to it, displaceable relative to the shaft 2. The balloon end of the urethral tamponading balloon portion, which extends beyond the urethral opening, can thus be compressed toward the glans in the manner of a bellows or its length can be adjusted.

Alternatively, an extension of the balloon envelope itself that is suitable for connecting a flexible supply line can be formed in the region of the proximal balloon envelope.

Figure 3B:
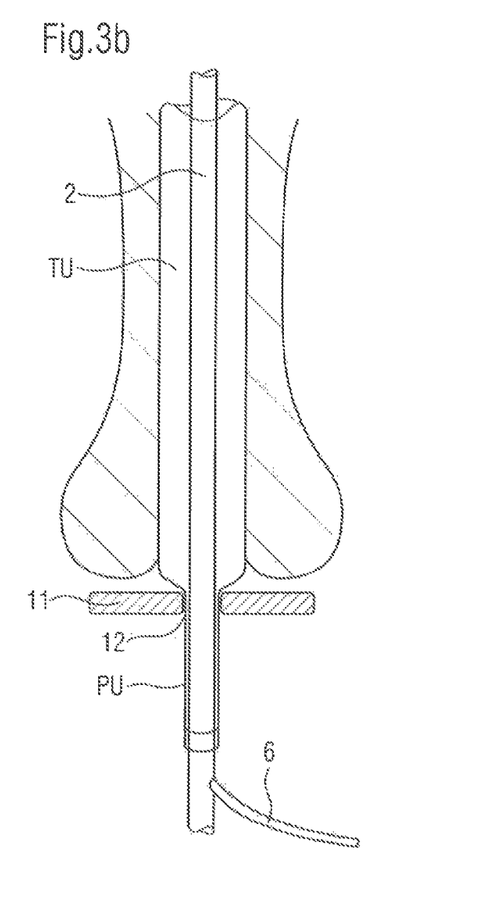
FIG. 3b a modified embodiment of the device described in FIG. 3a, wherein the proximal balloon end that extends beyond the outer orifice can be fixed or caught by a sleeve- or disk-like element.
Figure 3C:
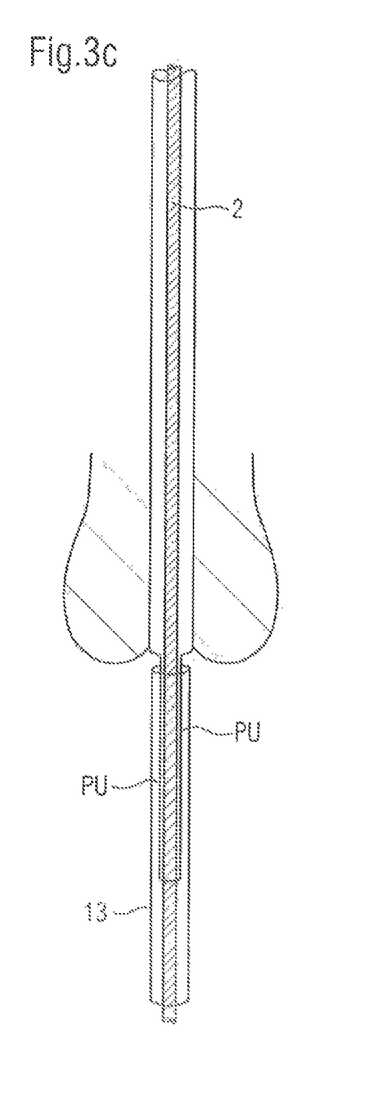

FIGS. 3b and 3c show two alternative embodiments which concern fixing the pre-urethral portion of the tamponading balloon 3 in place and cutting it to size. For one thing, according to FIG. 3b, the proximal balloon end can be provided with a disk 11 consisting of an elastic material and having a central opening 12, said disk being mounted on the catheter shaft 2 with sealing tension. By its pressing effect on the shaft, the disk 11 limits the pre-urethral expansion of the tamponading balloon and prevents the balloon portion proximal to the disk from filling. According to FIG. 3c, a sleeve-like elongate element 13 can be integrated into the device and is displaced from the proximal end of the shaft over the pre-urethral end of the balloon PU, and the area of deployment of the balloon envelope upstream of the urethral opening is limited in this way.

Figure 4A:
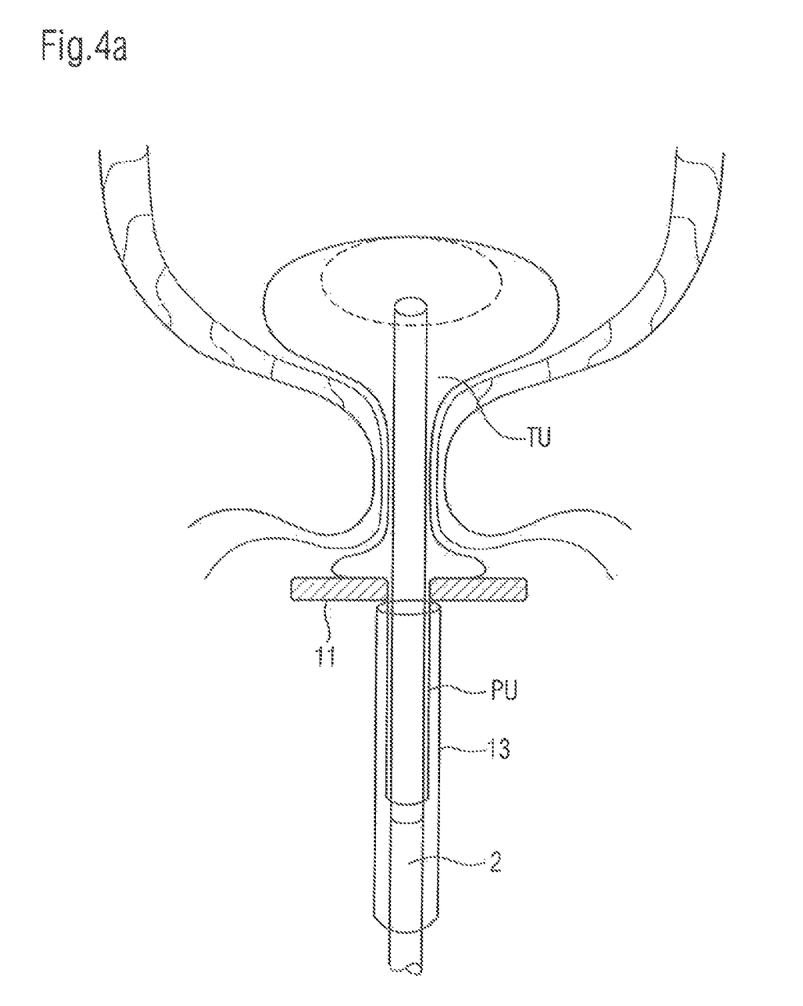
FIG. 4a an embodiment variant of the catheter for the transurethral sealing of the female urethra.

FIG. 4a shows a specifically shortened embodiment of the urethral tamponade TU for the female urethra. In this embodiment, the urethral segment TU preferably extends through the urethra. It has a length of 2 to 6 cm, preferably 3 to 4 cm. The proximal end of the trans-urethral segment TU transitions to a preferably spherical or discoidal expansion of the balloon envelope 14, which is deployed directly upstream of the outer urethral opening.

Because the length of the urethra varies among individuals, this embodiment is preferably equipped with a claimed element 11 and/or 13 which, as is shown in FIG. 3a, permit a pre-urethral sizing and fixation of the balloon envelope.

Figure 4B:
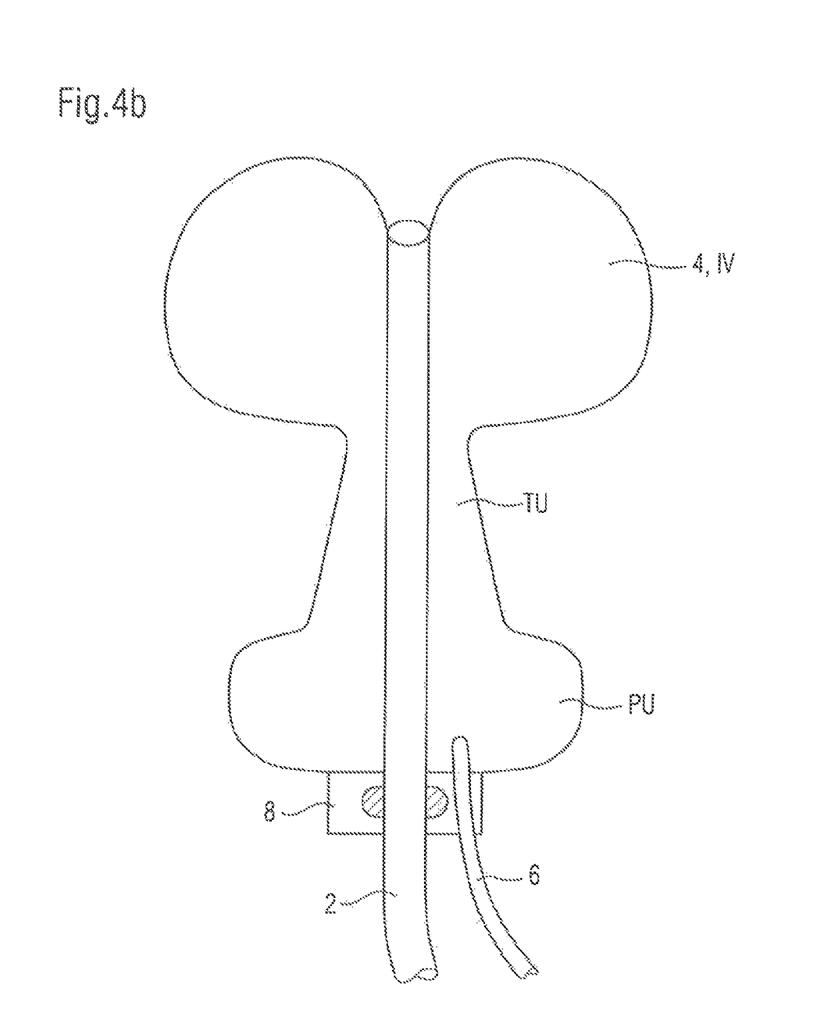
FIG. 4b a modification of the device described in FIG. 4a, with a conical embodiment of the urethrally tamponaded transurethral balloon segment.

Since the female urethra is generally similar in length but has a variable diameter, depending upon the individual sphincter tone, the invention proposes a conical expansion of the diameter of the trans-urethral segment TU extending from the inner entrance of the urethra to the outer outlet of the urethra, as is shown in FIG. 4b.

In the embodiments according to FIGS. 4a and 4b, the closure element 8 described in FIG. 3a, which can be displaced relative to the shaft body 2, can be used advantageously to receive the proximal end of the pre-urethral segment PU. It permits the length-adapting compression of the extracorporeal end toward the orifice, wherein the element 8 advantageously immerges into the pre-urethral, spherically or discoidally expanded segment and is thereby protected from direct contact with the sensitive orifice. The elements 11 and/or 13 for fixing the extracorporeal balloon in place or cutting it to size can likewise be combined with this design.

The embodiments described in FIGS. 4a and 4b can also advantageously be utilized for so-called supra-pubic catheters, in which the transcutaneous puncture channel is similarly tamponaded by a balloon extension that is adjacent to the vesical balloon portion. The techniques described in the invention for fixing the extracorporeal balloon segment in place and cutting it to size can be used here, as well.

Furthermore, the embodiments described in FIGS. 4a and 4b can be employed as a urethra closure device in cases of functionally insufficient sphincters and urinary incontinence. In this case, the draining shaft element can be replaced by a blind tubule, which in particular is designed to be so kink-resistant that it allows for self-catheterization by the patient. When the balloon body is correspondingly thin-walled with a thickness in the micrometer range, e.g. 5 to 15 µm, minimally irritating, easy-to-wear stopper-like closure products can be produced in particular for women with stress incontinence.

Figure 5:
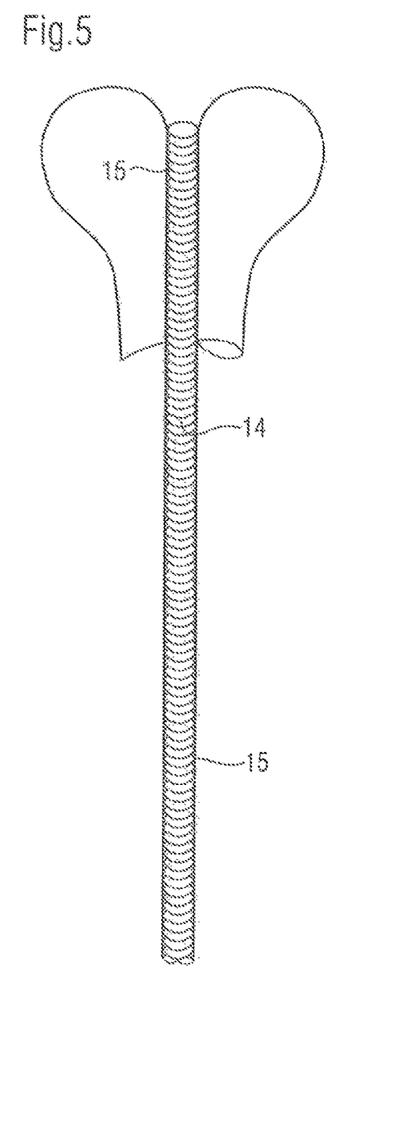
FIG. 5 a particular embodiment of a catheter shaft, wherein crystalline deposits on the inner and outer shaft surfaces can be avoided by the bellows-like corrugation of the shaft.

FIG. 5 shows a particular embodiment of a urine-discharging catheter shaft 14 which is made of an elastic material and which has walls that are provided with a wave-like profile 15 over the entire wall, wherein the profile gives the shaft bellows-like compression and extension mechanics. The intermittent axial stretching of the bellows-like shaft body 2 makes it possible to break off the crystalloid urine deposits, which lead to a progressive narrowing of the lumen during the course of drainage in conventional urine-discharging catheters, in a way that opens the lumen and to remove them from both the inner and outer walls of the catheter. If the pulling effect decreases, the shaft's particular elastic deformation property results in a prompt restoration of the bellows-like profile. The axial increase in the length of the shaft triggered by the axial pulling effect preferably arises even in response to small relative movements between the patient and catheter or minor tensile forces.

Figure 6:
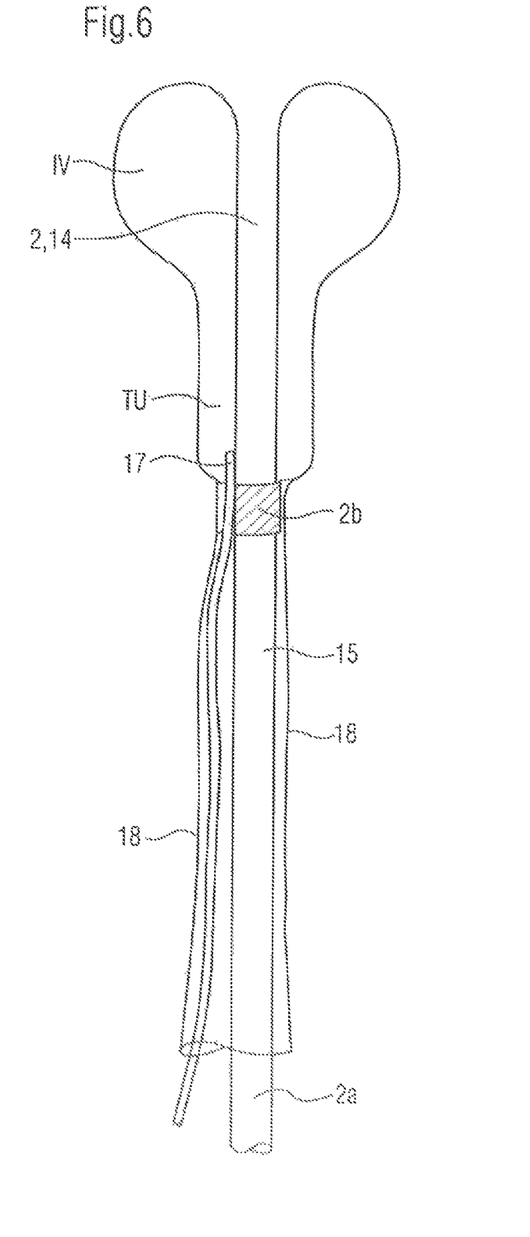
FIG. 6 a particularly cost-effective embodiment of the catheter, which is constructed out of a single continuously molded element.

FIG. 6 represents an embodiment of the urine-discharging device, the components of which are molded almost completely from one single material blank, preferably by blow molding. In so doing, the end of the molded balloon body 2a is inverted through the other end 2b of the balloon. The end 2b is then sealed to the surface of the end 2a that is elongated to the discharging tube. The claimed anchoring and sealing balloon body with a vesical IV and a transurethral portion TU is formed in this way. To configure the urine-discharging shaft portion 2 to be sufficiently kink-resistant and flexible, the shaft is provided with a wavy corrugation 15, in the manner of a corrugated tube, over its entire length or else only in some sections. For example, polyurethane types advantageous for balloon molding, having a higher durometer reading of 90 A to 95 A and 55 D to 65 D on the Shore scale can be used; when combined with a lumen-stabilizing, corrugated tube-like profile, these polyurethanes provide sufficient stability for the lumen in the shaft area, even in a thin-walled embodiment, as well as sufficient untensioned flexibility of the shaft. The molded shaft can comprise the following features, for instance: Outer diameter 3.5 mm, inner diameter 3.2 mm, polyurethane with Shore hardness 95 A, corrugation amplitude 0.7 mm, peak-to-peak spacing of the corrugation 0.5 mm. The molded balloon portion comprises: Wall thickness vesical –10 µm with a maximum diameter of 25 mm, wall thickness transurethral –20 µm with a maximum diameter of 10 mm. The balloon is filled preferably through a feed line 17, which is inserted into the joining region of the balloon end 2b on the shaft, between the shaft and balloon end, and empties here into the balloon. The feed line is preferably retained in an enveloping tubular film 18 that attaches to the balloon end 2b and preferably extends over the entire length of the shaft.

LIST OF REFERENCE SIGNS

1 Device
2 Shaft body
3 Balloon
4 Vesical balloon segment
5 Urethral balloon segment
6 Filling line
7 Display mechanism
8 Closure element
9 Opening
10 Annular sealing element
11 Disk
12 Opening
13 Sleeve
14 Catheter shaft
15 Wave-like profile
17 Feed line
18 Tubular film
IV Intravesical portion
BT Bladder trigone
TU Transurethral extension
TM Funnel outlet
TMV Funnel reinforcement element
PH Prostate resection cavity
TP Balloon envelope
TPF Bellows-like profile
F Fold
PU Envelope end

The invention claimed is:

1. A device in the form of a tube or catheter for draining or sealing a natural or artificial bladder outlet, comprising a shaft body that can be applied into a bladder of a patient, as well as a balloon that surrounds it like a cuff wherein the balloon comprises:
   a) an intra-vesical portion (IV) which is placed in the bladder of the patient for the purpose of a vesical anchoring of the shaft body in the bladder; and
   b) a urethral or trans-urethral portion (TU) which extends into a urethra or through the urethra of the patient for the purpose of a urethral or a trans-urethral sealing, wherein the urethral or trans-urethral portion of the balloon is pre-formed during manufacture from a material with a durometer reading of 70 A to 95 A and/or 55 D to 65 D on the Shore scale, with a "residual" diameter that exceeds a diameter of a urethral lumen of the patient by 0.5 to 1.5 times, and rests upon the shaft body in an only incompletely filled, flaccid state.

2. The device according to claim 1, characterized in that the balloon is configured with thin walls with a wall thickness from 5 µm to 15 µm.

3. The device according to claim 1, characterized in that the balloon consists of polyurethane, or of micro-thin-walled polyurethane with a wall thickness from 5 µm to 15 µm.

4. The device according to claim 1, characterized in that the balloon is already pre-shaped to its working dimensions during manufacture and that it rests upon the shaft body in an only incompletely filled, flaccid state.

5. The device according to claim 1, characterized in that an envelope of the balloon has a higher durometer reading of 90 A to 95 A and/or 55 D to 65 D on the Shore scale.

6. The device according to claim 1, characterized in that the intra-vesical portion (IV) of the balloon is bulbous or conical, wherein the tip of the bulb or cone is oriented toward a trigone (BT) of the bladder of the patient so that, when partially filled, it can snugly fit as well as possible in a situs of the bladder outlet.

7. The device according to claim 1, characterized in that the urethral or trans-urethral portion (TU) of the balloon is pre-formed with a "residual" diameter that exceeds the diameter of the urethral lumen of the patient by 0.5 to 1.0 times.

8. The device according to claim 1, characterized in that the balloon is or can be filled with a gaseous medium, in particular with air.

9. The device according to claim 7, characterized in that the anchoring intra-vesical portion (IV) of the balloon and the sealing urethral or trans-urethral portion (TU) of the balloon placed in situ is to be filled with an incomplete or partial filling medium, which is dimensioned such that the balloon as a whole remains in a flaccid state of expansion, i.e. that the balloon wall is not exposed to a permanent expanding force.

10. The device according to claim 1, characterized by a feed line, which is integrated into a wall of the balloon-supporting shaft body and which communicates with the balloon, for conducting a filling medium into the balloon.

11. The device according to claim 1, characterized by a feed line that opens directly into a proximal end of the balloon for conducting a filling medium into the balloon.

12. The device according to claim 1, characterized by a feed line gap between a proximal end of the balloon and an outer surface of the shaft body for conducting a filling medium into the balloon.

13. The device according to claim 10, characterized by a preferably terminal one-way valve, which is integrated into a feed line to the balloon and which opens when a filling syringe is applied and automatically closes when a syringe cone is removed.

14. The device according to claim 10, characterized by a manometric pressure display that is or can be attached to a feed line to the balloon.

15. The device according to claim 1, characterized by a filling pressure within the balloon on an order of magnitude of 10 mbar or 5 to 7 mmHg.

16. The device according to claim 1, characterized by an antibacterial coating on a surface of the balloon, or on a surface of the urethral or trans-urethral balloon portion (TU).

17. The device according to claim 1, characterized in that the balloon consists of a thin-walled tubing with a wall thickness from 5 µm to 15 µm, preferably made by blow molding from pre-extruded tubing.

18. The device according to claim 1, characterized in that the shaft body is made of polyurethane (PUR) and/or of materials with Shore hardness of 60 A to 90 A, preferably of materials in the hardness range 70 to 85 A.

19. The device according to claim 1, characterized in that an outer diameter of the shaft body lies in a range of 2 to 6 mm, or in a range of 3 to 5 mm.

20. The device according to claim 1, characterized in that a wall thickness of the shaft body lies in a range of 0.1 mm to 0.5 mm, preferably in a range of 0.15 mm to 0.3 mm.

21. The device according to claim 1, characterized in that the balloon consists of a single continuous balloon envelope.

22. The device according to claim 1, characterized in that the urethral or trans-urethral portion (TU) of the balloon has one or more balloon compartment(s) that attach to a vesical balloon in the proximal direction and are constructed of separated molded balloon elements, which are arranged together in direct succession.

23. The device according to claim 22, characterized in that a plurality of balloon elements are connected together and permit a communicating filling of the respective balloon compartment(s).

24. The device according to claim 22, characterized in that the vesical balloon segment is configured as a flat disk in a region of a bladder floor.

25. The device according to claim 22, characterized in that the vesical balloon portion is provided with a funnel-like outlet region in its distal region.

26. The device according to claim 25, characterized in that a film element (TMV) that stabilizes the funnel shape and is shaped accordingly is arranged in a region of a funnel-like section of the balloon, and/or is attached to the balloon.

27. The device according to claim 1, characterized in that a distal outlet (TM) of the shaft body is located proximally to a distal end of the balloon.

28. The device according to claim 1, characterized in that a transition from the intra-vesical balloon portion (IV) into a distal outlet (TM) of the shaft body is located at a same level as a transition of a bladder floor or bladder trigone (BT) into the urethra of the patient.

29. The system according to claim 1, characterized in that one end of the balloon is inverted through the other.

30. The system according to claim 1, characterized in that the shaft body element that is produced by means of shaping has a wavy corrugation, and so it has radial stability and kink-free flexibility.

31. The system according to claim 1, characterized in that both the shaft body and the balloon are formed from a single material blank.

32. The system according to claim 1, characterized in that a distal portion of the balloon is configured such that it corresponds to dimensions of a prostate resection cavity (PH) of the patient and preferably has a diameter that is residually dimensioned in this regard.

33. The device according to claim 32, characterized in that a distal end of the balloon, which is placed in the prostate resection cavity (PH) of the patient, does not project into the bladder of the patient but instead runs approximately flush with a bladder floor of the patient.

34. The device according to claim 1, characterized in that the urethral or trans-urethral portion (TU) is between 3 and 10 cm long, preferably between 5 and 8 cm.

35. The device according to claim 1, characterized in that a proximal end of the urethral or trans-urethral portion (TU) transitions to a preferably spherical or discoidal expansion (PU) of the balloon, which is deployed directly upstream of an outer urethral opening.

36. The device according to claim 35, characterized by a closure element, e.g. in the form of a disk and/or a sleeve, which is mounted on the shaft body like a cuff and which is disposed outside at the proximal end of the urethral or trans-urethral portion (TU) upstream of the spherical or discoidal expansion (PU).

37. The device according to claim 36, characterized in that the closure element can be displaced relative to the shaft body and can be arrested on it so that an extracorporeal end can be compressed toward an orifice of the patient in a length-adapting way, wherein the displaceable closure element advantageously immerges into the spherically or discoidally expanded segment (PU) and is thereby protected from direct contact with the orifice of the patient.

38. A device in the form of a tube or catheter for draining or sealing a natural or artificial bladder outlet, comprising a shaft body that can be applied into a bladder of a patient, as well as a balloon that surrounds it like a cuff wherein the balloon comprises:
- a) an intra-vesical portion (IV) which is placed in the bladder of the patient for the purpose of a vesical anchoring of the shaft body in the bladder; and
- b) a urethral or trans-urethral portion (TU) which extends into a urethra at least to, or beyond, the structures of the pelvic floor of the patient or through the urethra of the patient for the purpose of a urethral or a trans-urethral sealing, wherein the urethral portion of the balloon is pre-formed during manufacture from a material with a durometer reading of 70 A to 95 A and/or 55 D to 65 D on the Shore scale, with a "residual" diameter, that exceeds a diameter of the urethral lumen by 0.5 to 1.5 times, and rests upon the shaft body in an only incompletely filled, flaccid state.

39. A device in the form of a tube or catheter for draining or sealing a natural or artificial bladder outlet, comprising a shaft body that can be applied into a bladder of a patient, as well as a balloon that surrounds it like a cuff wherein the balloon comprises:
- a) an intra-vesical portion which is placed in the bladder of the patient for the purpose of a vesical anchoring of the shaft body in the bladder; and
- b) a urethral or trans-urethral portion which is between 3 and 10 cm long and extends into the urethra or through the urethra of the patient for the purpose of a urethral or a trans-urethral sealing, wherein the urethral portion of the balloon is pre-formed during manufacture from a material with a durometer reading of 70 A to 95 A and/or 55 D to 65 D on the Shore scale, with a "residual" diameter, that exceeds the diameter of the urethral lumen by 0.5 to 1.5 times, and rests upon the shaft body in an only incompletely filled, flaccid state.

\* \* \* \* \*